United States Patent [19]

Deutsch et al.

[11] E Patent Number: Re. 31,948

[45] Reissued Date of Patent: Jul. 16, 1985

[54] DENTAL POST AND WRENCH THEREFOR AND METHOD OF RESTORING BULK TO A TOOTH ROOT THEREWITH

[76] Inventors: Allan S. Deutsch, 345 E. 80th St., New York, N.Y. 10021; Barry L. Musikant, 222 W. 83rd St., New York, N.Y. 10024

[21] Appl. No.: 692,500

[22] Filed: Jan. 18, 1985

Related U.S. Patent Documents

Reissue of:

[64] Patent No.: 4,480,997
Issued: Nov. 6, 1984
Appl. No.: 568,082
Filed: Jan. 4, 1984

U.S. Applications:

[63] Continuation-in-part of Ser. No. 321,440, Nov. 16, 1981, abandoned.

[51] Int. Cl.[3] ..... A61C 5/04

[52] U.S. Cl. ..... 433/221

[58] Field of Search ..... 433/225, 221, 174, 175; 411/119, 422

[56] References Cited

U.S. PATENT DOCUMENTS

| | | | |
|---|---|---|---|
| 965,246 | 7/1910 | Stillman | 433/221 |
| 1,523,463 | 1/1925 | Thomson | 411/419 |
| 1,524,409 | 1/1925 | Simmons | 433/221 |
| 4,348,183 | 9/1982 | Weissman | 433/174 |
| 4,365,958 | 12/1982 | Vlock | 433/225 |

*Primary Examiner*—Robert Peshock
*Attorney, Agent, or Firm*—Bauer & Amer

[57] ABSTRACT

An improved unitary bulk restoring dental post having a stem of substantially parallel threaded sides divided along its length into separate legs for threaded insertion into a tooth root canal by a wrench that applies a predetermined torque to the dental post to thread it into the tooth root for crown restoration.

13 Claims, 13 Drawing Figures

DENTAL POST AND WRENCH THEREFOR AND METHOD OF RESTORING BULK TO A TOOTH ROOT THEREWITH

Matter enclosed in heavy brackets [ ] appears in the original patent but forms no part of this reissue specification; matter printed in italics indicates the additions made by reissue.

This application is a continuation-in-part of co-pending application Ser. No. 321,440, filed Nov. 16, 1981 and now abandoned.

This invention relates to an improved dental post for use in a tooth root canal to restore bulk to the tooth root for crown restoration.

Dental posts that were made in the past were generally of solid unyielding construction. Dental posts exemplifying such construction were made with tapered threaded surfaces as in the U.S. Pat. No. 4,239,489 to Ellman. Other posts were made with surfaces of continuous diameter substantially fully along their lengths as exemplified by the U.S. Pat. Nos. 3,524,255 and 3,656,236 to Kurer and also U.S. Pat. No. 3,861,043 to Lieb. Some dental posts even suggested a slot along the length of the side thereof as in the U.S. Pat. No. 644,804 to Justi. The U.S. Pat. No. 838,296 to Best and the aforenoted patent to Ellman disclose hollow posts. The U.S. Pat. No. 4,234,309 to Sellers exemplifies the teaching of the combination of a wrench for use with a dental post, while the Swiss Pat. No. 562,605 is substantially to the same effect wherein the threads on the dental post stop short of the leading end of the post where the greatest retentive force is achieved. Simmons U.S. Pat. No. 1,524,409 teaches corrugated forked members each of which is non-threadedly implanted in a separate bifurcation of a dental root.

The teachings of the dental post of the prior art are that when the post is threaded into the root canal of the tooth, the forces applied by the thread of the post against the engaging walls of the tooth exert outward expansive forces to the tooth root and that, at times, cause the same to fracture. Fractured teeth are irreparable and, therefore, it is important to prevent the fracture of the tooth root during the threading application of the dental post thereinto, and even during the subsequent use of the tooth after the dental post and crown have been assembled to the root.

Dental posts of the type disclosed in the prior art have also resulted in the fracture of the tooth root by reason of lateral forces and stresses applied to the post during mastication.

Prior to the present invention, dental students and practicing dentists and especially specialists in the art of endodontics as well as teachers, professors, researchers and writers were taught and continue to teach that a dental post must be rigid and inflexible. Because of such teachings prior to the present disclosure, it was believed that when a flexible or non-rigid dental post was implanted in a tooth root canal, it would not provide the required rigidity and support to the tooth that the tooth needs to resist the stresses and forces to which it is subjected.

The aforementioned problems of the prior art dental posts are solved by the present invention. The present invention provides a dental post that generates its own thread as it is threadedly inserted into the tooth root canal and because its relatively spaced threaded legs move radially to absorb the self-tapping threading torque and other forces it prevents the application of such forces and stresses to the walls of the tooth root so as to permit the dental post to be threaded thereinto without fracture to the tooth. While the dental post taps and is threaded into the tooth, it is anchored by cement applied to the root canal so as to prevent the occurrence of anti-rotational or unthreading forces that might normally tend to cause the post to unthread from its seat in the root of the tooth. Such anti-rotational or unthreading forces are countered by the normal radial expansion and tangential movement of the threaded legs of the dental post into tighter frictional wedging engagement with the wall of the tooth root canal. They are further prevented by the cement that anchors into dentinal wall irregularities and in the slot between the legs. Further, displacement and venting of the cement, debris, fluids and build-up of hydrostatic forces from between the post and the root canal is provided for.

The above description, as well as further objects, features and advantages of the present invention, will be more fully appreciated by reference to the following detailed description of a presently preferred, but nonetheless illustrative, embodiment in accordance with sthe present invention when taken in conjunction with the accompanying drawings wherein.

Figure 1:
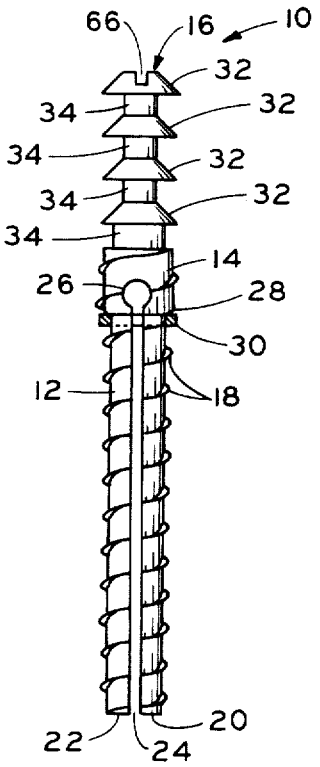
FIG. 1 is an enlarged plan view of a dental post constructed according to the invention.
Figure 2:
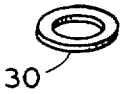
FIG. 2 is a perspective view of a shock absorbing element for use with the dental post of FIG. 1.
Figure 3:
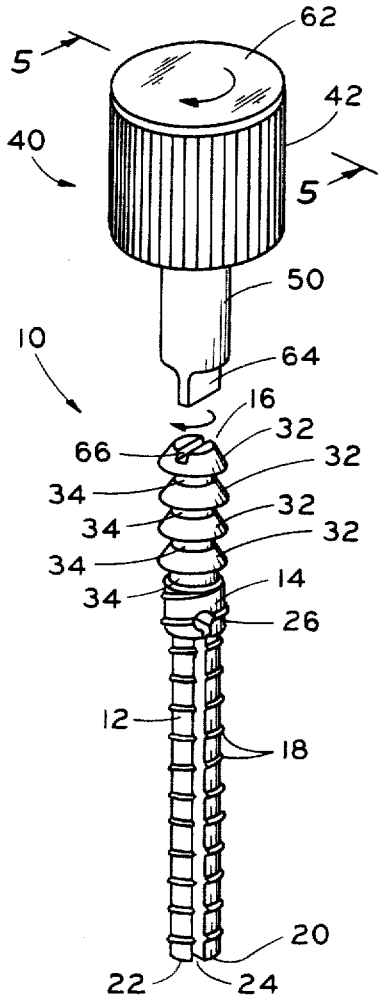
FIG. 3 is a perspective view of the dental post of FIG. 1 and shown in combination with a torque wrench according to the invention.

Referring now to FIGS. 1, 2 and 3 of the drawing, the dental post there illustrated is generally identified by the numeral 10 and comprises a stem 12 formed unitarily with a body 14 and a crown anchoring means generally identified by numeral 16. The stem 12, body 14 and crown anchoring means 16 all are integrally connected together and formed as a unitary structure with a thread 18 provided on the stem and body. Hence, although the parts are separately identified, none of them is intended to be normally capable of separation from the other.

In the event the stem 12 is of an elongated length that is greater than that of the length of the root canal into which the same is adapted [to top a thread and] to be threadedly inserted, it may be cut short [at its apical or insertion end] to the length of the root canal by a dental diamond wheel. After pulp is removed from the root canal 19 and the canal is obturated, it is reamed to a diameter corresponding to that of the stem wall 12, but left unthreaded.

The stem 12 is divided or separated into a desired plurality of legs exemplified in the drawing by the two legs 20 and 22 relatively spaced by a through space or slot 24 that extends fully along the length of the stem and therebeyond into the body 14 to terminate in an enlarged curved opening 26. By providing the end of the slot 24 with the curved termination 26, the same obviates the possibility of fracture occurring at the closed end of the slot 24 when compressive forces are applied to the legs 20 and 22 in a manner to be described.

Not only does the enlarged termination 26 of the slot 24 eliminate the possibility of fracture of the dental post 10 at the end of the slot, it also provides a means by which the legs 20 and 22 of the stem of the post are permitted to flex and move relative to each other so as to permit the same to collapse toward each other in a radial direction and to skew arcuately and move tangentially relative to each other. Thus, the connection between the legs 20 and 22 afforded at the surface surrounding the enlarged excavation or termination end 26 of the slot functions as a spring-like joint about which the legs flex and yield.

As will become apparent, the space of the slot 24 provides room sufficient to permit the legs 20 and 22 to move radially and tangentially toward and away from each other. It also serves to permit the legs to absorb radial forces that are applied to the legs when the same are threaded into the root canal 19 of the tooth root 25. The ability of the legs to flex and move relatively radially and tangentially toward and away from each other enables them to create and form their own thread and to conform to the irregularities of the thread 18 they generate in the root canal 19. This movement permits the legs to absorb stresses and forces that would otherwise be applied to the walls of the root canal 19 to cause the tooth 25 to fracture in response thereto.

As will also become apparent, the lengthwise extent of the space or slot 24 between the legs 20 and 22 terminates at a point 26 that is within the body 14 and provides a unique advantage over the prior art. The space of the slot 24 affords a vent for cement and dental debris and releases hydraulic and pneumatic forces that normally tend to build up beneath and about the dental post 10 as the same cuts its own thread and is threaded with cement into the root canal of the tooth. The space of the slot 24 that enables relative movement of the legs, and being longer in length than the stem 12, now effects a path of escape from the bottom of the root canal 19 of the tooth 25 and from beneath the leading or insertion end of the step 12 upward to the surrounding atmosphere. The space 24 enables accumulation of the debris, air, fluids and gases therein and to exhaust the same from the canal 19 without damage to the tooth root.

The thread 18 of the stem 12 extends for the full length thereof and for the full length of the larger widthwise dimensioned body 14. The body 14 may have its lower end 28 tapered or curved in the manner as illustrated in FIG. 1 so as to permit the same to conform substantially to the taper or curve of the complementary countersunk tooth root 25 into which the stem and body are to be threaded. Thus, when the stem 12 and body 14 are fully threaded into the tooth root canal 19, the tapered or curved end 28 of the body 14 will engage the inner countersunk surface of the tooth to fit and seat conformingly thereagainst in a non-stressing manner. The larger threaded body 14 fits snugly within the countersunk coronal aspect to provide a full and larger wall-to-wall surface retentive engagement therewith. This avoids the application of lateral outward stressing forces against the engaged surface of the tooth root 25 that might otherwise tend to fracture the tooth when so engaged by prior art dental posts.

Although it has been found in practice that the conforming shape 28 of the body 14 avoids fracture of the tooth root when the same engages therewith, it is within the contemplation of the invention that an elasticized washer or seal 30 shown more clearly in FIG. 2 may be utilized with the dental post 10. The washer or seal 30 may be made of any desired elastic or yieldable material, as silastic. When the washer 30 is threaded upward along the threads 18 of the stem 12, it stops in its abutment with the underside of the body 14 adjacent to the curved or tapered surface 28 thereof.

When the stem 12 and body 14 are threaded into the tooth root canal 19 to their full extent thereof, the washer 30 is compressed in its engagement within the coronal aspect of the tooth root 25 to form an air-tight seal between the tooth root and the surface 28 of the body 14. When so engaged and compressed, it also functions as a shock absorber to resiliently absorb the stresses and forces that are otherwise applied during the threading of the tooth post 10 into the tooth root canal 25. After the post 10 is threadedly implanted in the tooth root canal 19 and a crown 31 is built and anchored about the root and about the anchoring portion 16 of the dental post 10, the sealing washer 30 functions to absorb the stresses and forces that are applied to the crown 31 and to the tooth root 25 by way of the dental post 10 during mastication and other grinding movements of the tooth.

The washer or seal 30 may be omitted from the dental post 10 in certain instances when the seat and fit effected between the body 14 and the root 25 is deemed sufficient and adequate without it. Under other conditions of use it may be desirable to include the washer 30 to provide for the effective seal and force absorption.

After the post 10 is securely threaded within the tooth root 25, it provides sufficient restoration of bulk to the tooth root to enable a crown to be restored to the tooth root about the anchoring means 16. The anchoring means hereshown is generally identified by the numeral 16 that extends outward of the tooth root in a direction opposite the threaded stem 12.

As illustrated in the drawing, the anchoring means 16 comprises a series or plurality of truncated cones 32 each of which is separated from the other along the length *of the* dental post 10 by integrally connected and unitarily formed extensions or separators 34. Each of the truncated conical elements 32 is provided with the larger diameter of its outer tapered surface directed toward the stem end of the post that is adapted to be threaded into the tooth root canal 19 or facing the stem 12. This downward and outward direction of the tapered surfaces of the cone elements 32 enhances the use of the post 10 in a manner to be described. In the event the height of the anchoring means 16 is greater than that required for crown restoration, the same may be shortened in length simply by grinding away as many of the trucated conical anchoring elements 32 and separators 34 that are found to be excessive and unnecessary.

The threaded application and insertion of the stem 12 and body 14 into tooth root canal is accomplished in a self-tapping manner to form the root canal thread 17, the sides of which are substantially parallel and conform precisely to that of the self-tapping thread 18 and the outer sides of the stem 12 and body 14 of the dental post 10. Dental cement is flooded into the root canal 19 and may also be applied to the stem 12 and body 14 so as to be in intimate contact with all the surfaces of the thread 18. Although the stem is shown to be divided into a plurality of two legs, it is within the scope of the invention that the stem may be divided into any number of legs formed by similar venting spaces or separations 24 therebetween. After the cement is applied to the stem 12 and body, the same is ready to be threadedly inserted into the tooth root canal 19.

In accordance with prior known procedures, this has been done by hand or with the use of a tool for rotating the dental post 10 downward along the threaded or unthreaded tooth root canal. It has been found that the application of too great a torque to the dental post 10 will tend to fracture the tooth if the same exceeds the lateral strength of the tooth root or the resisting force the tooth exerts against the stem 12 and the body 14 as the same is threaded thereinto. Hence, it is within the contemplation of the present invention that the dental post 10 be threadedly inserted into the tooth root canal by means of a releasable torque wrench generally identified by the numeral 40 illustrated in FIGS. 3 and 5. The wrench 40 is capable of applying a threading torque to the post 10 that will be less than the fracture resisting strength of the tooth root.

Figure 5:
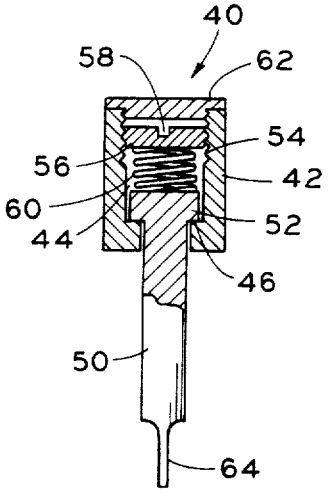
FIG. 5 is a vertical cross section of FIG. 3 taken substantially along lines 5—5 thereof.

The torque wrench 40 comprises a manually rotatable driving handle 42, the interior of which is hollowed to form a chamber 44 as is shown in FIG. 5. The lower end of the chamber terminates in a closure wall 46 that has a centrally located opening 48 through which a driven shaft 50 extends outwardly from the handle 42. The driven shaft 50 has an enlarged head 52, the undersurface of which provides a clutch or engaging surface that engages with the facing engaging surface of the wall 46. The engaging surfaces of the head 52 and wall 46 function as clutch means to transmit the drive from the drive head 42 to the driven shaft 50. The surfaces are relatively smooth and, therefore, enable the surfaces to slip with respect to each other when the same is desired and required.

The interior chamber 44 of the handle 42 is threaded as at 54 to receive a threaded adjustment element in the form of a nut 56 that may be conveniently provided with a screwdriver receiving slot 58 therein. Contained between the adjustment element 56 and the head 52 of the driven shaft 50 is a yieldable urging or force applying means in the form of a spring 60. The spring 60 is trapped between the adjustment element 56 and the head 52 and is variable in tension by the adjustment of the element 56 within the chamber 44 of the driving housing 42.

The wrench interior may be closed against undesired tampering by the application of a closure cap 62 applied to the thread 54. The driven end of the shaft 50 may be provided with any convenient engaging means to drive the dental post 10 during its threaded rotation into the tooth root canal. For convenience of illustration and understanding, the same is shown to have a very simple screwdriver blade 64. The dental post 10 is provided at the top thereof with a complementary engaging slot 66 to receive the blade 64. Those skilled in the art will recognize that other cooperating engaging arrangements of structures may be provided to accomplish the torque limiting teaching of the present invention. Prior to the self-tapping threaded insertion of the dental post 10 into the tooth root canal 19, the adjustment nut 56 of the torque wrench 40 is adjusted to compress the spring 60 to apply a predetermined yieldable force against the head 52 of the driven shaft 50 to force the same into surface-to-surface engagement with the wall 46. After the torque wrench 40 is adjusted, the same is now ready for use.

The stem 12 of the dental post is aligned with the tooth root canal 19. The initial rotation of the dental post 10 may be accomplished by the fingers of the hand to set the dental post and its stem 12 into the canal 19. Thereafter, the dental post is more fully self-tappingly threaded into the tooth root 25 by the use of the torque wrench 40 by placing the blade 64 of the torque wrench into engagement with the receiving slot 66 of the dental post 10 and rotating the handle 42.

As the stem 12 and the body 14 thread themselves progressively into the root canal 19 and form the thread 17, whatever fluids, debris, gases or air trapped beneath the leading or insertion end of the stem are accommodated or vented to the atmosphere during such self-tapping insertion in a manner as previously discussed until even the connection 26 is finally encompassed within the orifice end of the canal 19. The spring-like connection formed between the legs 20 and 22 permits the legs to flex inward radialy toward each other conforming to and absorbing irregularities that may occur during the engagement of the threads 18 with the root canal 19. In this manner, whatever fracture producing forces that may occur during such threaded engagement are now absorbed by the radially inward yielding of the legs toward each other as afforded by the slotted space 24 therebetween. The connection 26, having a memory, acts in the nature of an outwardly urging spring, constantly causes the threads 18 of the stem 12 and body 14 to move radially outward into full contacting threaded engagement with the threads 17 they form in the root canal 19. This assures that at all times the fullest benefit of the threaded engagement between the two threads 17 and 18 is afforded.

Figure 7:
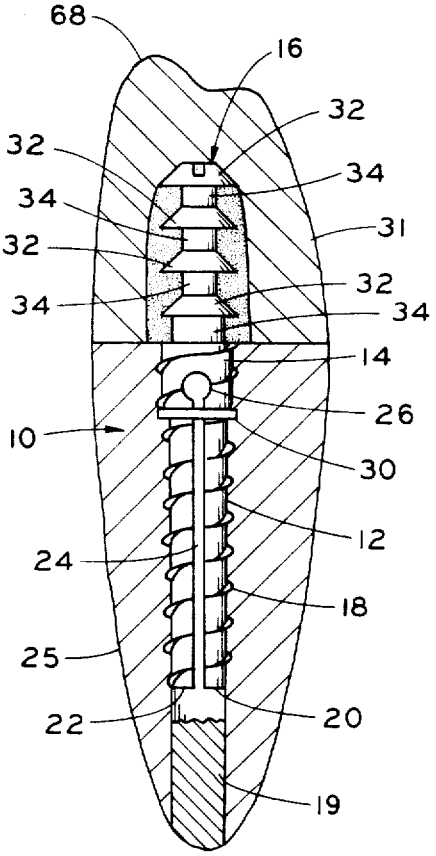
FIG. 7 is a smaller scale plan view of a dental post of the invention threaded in a tooth root and crown thereon[;].
Figure 9:
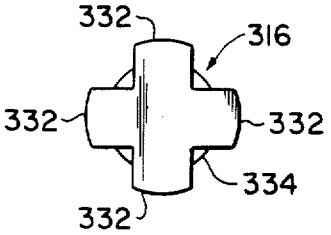
[FIG. 9 is a view of the distal or anchoring end of FIG. 8;]
Figure 8:
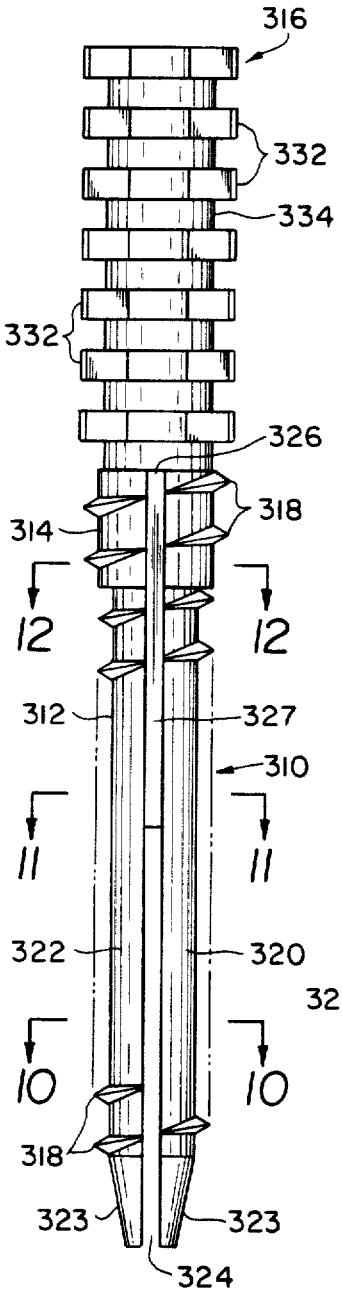
[FIG. 8 is an enlarged plan view of another dental post constructed according to the invention;]
Figure 12:
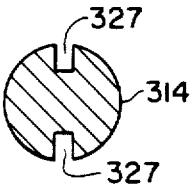
[FIG. 12 is a cross section of FIG. 8 along lines 12—12; and]
Figure 11:
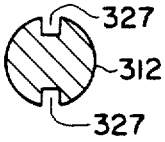
[FIG. 11 is a cross section of FIG. 8 along lines 11—11;]
Figure 10:
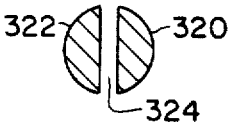
[FIG. 10 is a cross section of FIG. 8 along lines 10—10;]

When a sealing type washer 30 is utilized, as is illustrated in FIG. 7, the same will be compressed between the exposed wall of the tooth root and the body 14 to fully seal the space therebetween and to provide a shock absorber thereat. When the sealing washer 30 is omitted, the adjacent surface of the body 14 will come into full surface-to-surface abutment and wall sealing engagement within countersunk wall of the tooth root canal 19.

Although the dental cement previously applied to the stem 12 and body 14 and its threads 18 is sufficient to retain the same in cemented frictional engagement with the tooth root canal 19, when the cement hardens, any tendency upon the part of the dental post 10 to reversely rotate outward of the tooth root 19 at a later time is resisted by the radial outward spring-like force applied to the legs 20 and 22 at the spring-like connection 26 therebetween. This causes the sharp slotted edges of the legs to move tangentially into wedging engagement with the wall of the root canal 19 to resist reverse threading. Thus, the spring-like connection 26 affords a memory that tends to return the legs 20 and 22 into full surface contact and anti-rotative engagement with the threads 17 of the tooth root canal 19.

If during the threading of the stem 12 and body 14 into the root canal 19 resisting forces occur that exceed that of the preset force of the spring 60 in the torque wrench 40, the spring 60 will permit relative slipping movement between the wall 46 of the handle 42 and the adjacent engaging surface of the head 52 of the driven shaft 50. As a consequence, until such times as the resisting force occurring between the threads 17 and 18 is removed or safely reduced, it will not be possible to continue to thread the stem 12 and body 14 into the root canal 19 by the use of the torque wrench 40. Accordingly, rotation of the torque applied to the dental post 10 through the driven shaft 50 will terminate. No amount of continued rotation of the handle 42 will cause the post 10 to thread deeper into the root canal 19 until such time as the fracture producing resisting forces exerted thereon are removed.

From what has been disclosed, it will be clear that once the adjustment of the element 56 in the torque wrench handle 42 is made so that the spring 60 will not apply a predetermined frictional engagement between the head of the driven shaft 50 and the surface of the wall 46 of the handle 42 that will exceed the strength and fracture resistance of the tooth, the tooth will not fracture during use of the wrench 40. No amount of continued rotation of the driving handle 42 will result in continued threaded engagement of the stem into the tooth root 19 because the clutch surfaces will slip and rotate relative to each other without transmitting drive therebetween. Therefore, even though the stem 12 and body 14 are capable of absorbing fracture producing stress forces applied between it and the tooth root 19, the use of the torque wrench 40 provides further assurance that at no time during the use of the same with the dental post 10 will the dental post exert a force on the tooth root 25 that will exceed the strength of the tooth root.

After the dental post 10 is applied to the tooth root 25 in the manner as described, the same is now ready for the application of a crown 68 to the tooth root 25 at the anchor means 16 of the dental post 10. The crown 68 is constructed in the conventional manner to provide a precise fit with the tooth root 25. It is provided with the conventional hollow interior that is intended to be circumpositioned about and over the anchoring means 16.

The crown 68 is shown schematically in FIG. 7. Its details of construction may be changed and are not necessarily limited to those here illustrated. Before the application of the crown 68 to the anchoring means 16, a dental or composite cement is applied to the interior thereof. Dental or composite cement may also be applied about the exposed surfaces of the truncated conical anchoring elements 32 and about the separators 34 and the body 14 of the dental post 10. The multi-truncated cone anchoring means 16 is unusually well adapted for use in restoring old or prior used bridgework and crowns.

Previously it was noted that the narrow diameter ends of the truncated cones 32 extend in a direction away from the stem 12 and toward the interior opening of the crown 68, while the larger diameter ends of the cones 32 extend downward toward the body 14 and the stem 12. The undersides of the larger diameters of each of the anchoring cones 32 function as surfaces beneath which the dental or composite cement flows and against which the same hardens in engagement therewith. They are tapered in the manner as illustrated and described to provide a natural flow of the dental cement in a direction from along the narrower portions of the truncated anchoring cones 32, along the enlarging surfaces and then into the spaces afforded by the separators 34 between each of the cone elements.

In practice, it has been found that when the dental cement is compressed, it flows along the path of least resistance from the narrower ends of the truncated anchoring cone elements 32 toward the larger ends and then into the spaces afforded by the separators 3 therebetween. The initial application of the dental cement in such spaces afforded by the separators 34 is even more fully compressed upon and during the application of the crown 68 over the whole of the anchoring means 16. The forces applied by the crown cause the cement to flow into all of the spaces that exist beneath the larger diameters of the truncated cones 32 so as to come into full and cementing engagement therewith. This assures a proper long-lasting connection and engagement between the crown 68 and the anchoring means 16 and the elimination of air pockets within the crown.

Figure 4:
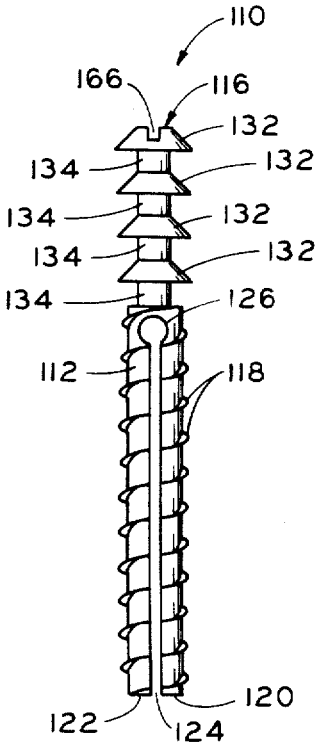
FIG. 4 is an enlarged plan view of another embodiment of the dental post.

The embodiment of the dental post shown in FIG. 4 is generally identified by the numeral 110. The 10's digits used in this embodiment correlate with like elements of structure described with respect to the embodiment 10 shown in FIGS. 1 and 3 and described with respect thereto. Therefore, for convenience all numerals used in connection with the description of the embodiment 110 of FIG. 4 will be identified in the 100 series.

FIG. 4 differs from that of the embodiment 10 previously described in its omission of the two-tier body 14 therefrom. As distinguished from the prior embodiment, the post 110 is unusually well adapted for use with multi-rooted teeth in which two or more such posts 110 may be used. The embodiment 110 comprises a threaded substantially parallel sided stem 112 whose thread 118 extends about each of the plurality of legs 120 and 122. As in the embodiment 10, the legs are divided and spaced from each other by a venting slot 124 that extends for a substantial length of the stem and terminates adjacent the end remote of the stem at the enlarged spring-like memory returning connection 126.

In the embodiment 110, the lengthwise extent of the stem 112 is such that its coronal end terminates at the orifice opening of the root canal 19. In like manner, the spacing slot or vent 124 provides an adequate *vent to the atmosphere from the leading or insertion* end of the stem 112 during its self-tapping insertion into the canal 19 until the connection 126 is finally [closed] *enclosed* in the root canal.

The dental post 110 is of unitary construction and includes crown anchoring means 116 that is constructed and functions in essentially the same manner as the crown anchoring means 16 of the embodiment 10 previously described. For this reason, a detailed repetitious description of the same will be omitted.

To assure that the dental post 110 is properly self-tapped and threaded into the tooth root canal 19 with the application of a torque thereto that does not exceed the strength of the tooth 25, the torque wrench 40 may be utilized in the manner as previously described with respect to the embodiment 10. To enable the use of the wrench 40, the embodiment 110 is provided with a complementary screwdriver slot 166 that is adapted to receive the screwdriver type blade 64.

It will be recognized by those who are skilled in the art that the mere illustration and description of the complementary shaped blade 64 and slot 66 shall not constitute a limitation upon the scope of the invention. Any other complementary engaging means may be used to effect the self-tapping and threaded engagement of the dental posts of the invention with the root canal 19 with a force that will not exceed the strength of the tooth root 25.

Figure 6:
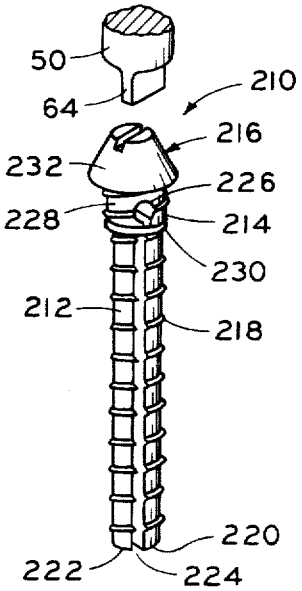
FIG. 6 is an enlarged perspective view of another dental post; *and*

Referring now to FIG. 6, the embodiment there illustrated corresponds in many of the essential details to that of the embodiment 10 described with respect to FIGS. 1 and 3. Hence, like details of construction are identified with the same 10's digits, with all of the numerals distinguishably numbered in the 200 series.

The similarity of the embodiment 210 with that of the embodiment 10 should at once become apparent. The stem 212 thereof terminates in the body 214 and both are slotted at 224 to provide the plurality of legs 220 and 222 that are separated and spaced for relative yielding movement with respect to each other to absorb shock and forces that might be applied to the self-tapping threads 218 thereof during the self-tapping threaded insertion and engagement of the dental post 210 with the root canal 19.

As with the prior described embodiments, the embodiment 210 is of unitary construction that includes a body 214 in which the defining walls of the enlarged opening 226 function to retain the memory of the separation of the plurality of legs 220 and 222. It also provides accommodation for debris and for venting to the atmosphere from the insertion end of the stem 212 during the threading of the stem and body into the complementary countersunk coronal aspect of the root 19. As illustrated in FIG. 6, the embodiment 210 may utilize a silastic washer or seal *230* as described with respect to the embodiment 10.

The embodiment 210 differs from that of the embodiment 10 in the details of the anchoring means 216. The embodiment 210 is unusually adapted for use with new crown restoration. For this reason, the anchoring means 216 eliminates the plurality of relatively spaced truncated cone anchoring elements 32 and combines it into a single smooth-sided truncated cone 232. Its narrower end is spaced remote from that of the stem 212 while its larger end faces in the direction of its unitary connection with and extension of the body 214.

The use of the dental post 210 is accomplished substantially in the same manner as previously described with respect to the prior embodiments. With respect to the post 210, the anchoring element 232 is provided with a slot 266 that will receive the end 64 of the driven shaft 50 of the torque wrench 40. The application and threaded insertion of the stem 212 of the dental post 210 into the threaded root canal 19 is accomplished in the same manner as previously described for the use of the torque wrench 40.

The blade 64 is engaged in the slot 266 of the anchoring element 232 to rotate the same into the tooth root canal 19. If at any time during such self-tapping threaded engagement forces are applied to the legs of the stem 212 that exceed the force exerted by the spring 60 in the torque wrench 40 as predeterminately set by the adjustment of the adjustable nut 56 therein, the clutch surfaces engaging between the wall 46 and the head 52 will slip and be permitted movement relative to each other. This assures that at no time will the application of torque to the dental post exceed the strength of the tooth 25 nor will the same exert fracture producing forces against the walls of the root canal 19 thereof.

As previously described, the legs 220 and 222 will flex and move relative to each other independently in response to whatever forces are exerted upon them during such self-tapping and threading operation. This ability of the legs of the stem to yield in response to the thread generating and threading forces enable the same to function as a shock and force absorber that transfers such forces to the stem legs for absorption thereby. In the absence of such force absorber, the forces are exerted outwardly against the new threaded wall of the tooth root canal 19 and will fracture the tooth 25 if the forces exceed the tooth strength.

In each of the embodiments the plurality of legs are normally spaced from each other by the slot formed between them. In each case the legs will yield relative to each other in response to forces applied to them to conform to irregularities encountered in their self-threading movement along the tooth root canal 19.

In each instance, the spring biased connection afforded by the walls surrounding the larger opening 26, 126 and 226 at the remote end of the slot exerts a returning force on the legs to cause them to tend to assume their normal parallel relationship. This outward urging force exerted at the spring connection 26 causes the threads 18 of each of the dental posts into fuller and more complete engaging relationship with the complementary surfaces of their formed threads 17 of the tooth root canal 19. The spring action of the legs uniformly allows them to absorb stress along their entire lengths and the slotted portion of the body. This results in greater cooperation and retention between the bulk restoring dental post and their formed threads 17 of the tooth 25. This fuller and greater extent of engagement also inhibits the anti-rotation or possible accidental disassembly of the dental post from the tooth root canal 19, while at the same time providing for complete shock and force absorbing engagement therebetween.

[Referring to the dental post of FIGS. 8 to 13 inclusive the same is generally identified by the numeral 310. As in the prior described embodiments, the 10's digits here used will identify the elements of structure used to identify like elements of each of the prior described embodiments. For convenience, all numbers here used will be in the 300 series.]

[The embodiment 310 of FIGS. 8 to 13 includes a body 314 coextensive and formed unitary with a stem 312 at its apical or insertion end and with a crown anchoring means 316 at its opposite or distal end. The stem 312 has an apical or leading end that is tapered from the terminal end of the threads 318 that are formed on each of the legs 320 and 322 produced by the space of the slot 324. It will be seen that the full extent of each of the tapered entry or apical ends 323 are free of threads but are angled to correspond to that of the angle of the leading end of the tooth root canal 19.]

[The function of the unthreaded apical ends 323 will become clearer as the description proceeds. However, at this point it is noted that the same provide aligning means by which the thread generating threads 318 are aligned with the root canal 19 when the stem 312 is introduced into the root canal. They also function to fit into and to fill and occupy substantially the full depth and area of the previously drilled root canal 19. Because the angle of the apical lead ends 323 correspond in angular relationship with the taper produced in the root canal 19 by the drill used to produce the root canal, the same will fill the end thereof substantially fully below the threads 318. This provides a longer post to root canal contact between the post 310 and the canal 19 to add additional strength to the tooth 25 by providing a greater length of stress absorption and distribution of forces.]

[The space of the slot 324 extends for a substantial length of the stem 312 to assure the legs 320 and 322 thereof will be able to move radially independently and tangentially relative to each other to perform the described flexing and relative movements as the self-tapping thread 318 generates the thread 317 in the tooth 25 during the threading of the past 310 thereinto. Although the space of the slot 324 is shorter in the present embodiment 310 than in the prior embodiments, the stem 312 and body 314 are provided with at least a venting continuation and extension groove 327 of the venting space 324. At least one or more venting spaces 324, 327 may be provided on the stem 312. The vent spaces 324, 327 perform the same venting function as was previously described with respect to the venting spaces 24, 124 and 224 kof the prior described embodiments since, as will be seen, the same extends kuninterruptedly from the apical end of the stem 312 to at least the distal end 326 of the body 314.]

[Hence, when the post 310 generates its own thread as it is threaded into the root canal 319, the distal end 326 of the combined vent 324, 327 always is exposed at the top of the root and tooth 25. This assures that the cd cement, debris produced by the cutting of the threads, fluids, air and other gases and pressure building materials are vented and exhausted to the atmosphere from the deepest apical end of the tooth root canal to prevent damage to the tooth root. As in the prior described embodiments, the space 324, 327 vents from the root canal any possible build-up of damaging hydrostatic pressure from beneath and about the apical end 323 of the post 310 as the post is self-tapped and threaded into the root canal 19.]

[As in the prior described embodiments the anchoring means 316 is provided to enable a crown to be mounted to the post 310. The present anchoring means is of general cruciform shape with a plurality of diametrically opposed anchoring lobes 332. Each of the sets of anchoring lobes 332 are relatively axially and longitudinally spaced from the other along the length of the anchoring means 316 by separators or spacers 334. Those skilled in the art will recognize that the selection of four lobes as is shown in the drawing is but a matter of choice. Any other number of lobes may be utilized. Four have been selected for illustration to permit the use of a torque wrench to rotate the dental post thereat.]

[The use and operation of the dental post 310 is essentially the same as that previously described with respect to the prior discussed embodiments. The benefits of the tapered apical leads 323 of the present embodiment may be readily utilized in the posts of the prior embodiments by providing each of them with such apical leads.]

[When in use, the present embodiment 310 provides a unique advantage over prior art dental posts in that it takes into consideration the need to assure the continued presence of a sufficiently thick body of dentin between the outer wall of the tooth and the post 310 that is threaded into the root canal 19. In the use of prior art dental posts little, if any, concern was given to the details of the dental post construction as to assure the continued existence of a sufficiently thick tooth root wall capable of resisting fracture of the tooth after the post tapped the same and was threaded thereinto.]

[The present invention takes into account such problems of fracture by arranging the details of structure of the dental post 310 to assure that there always exists at least a minimum tooth wall thickness of not less than one mm. between the outer wall of the tooth and the nearest adjacent detail of dental post structure. To this end it will be seen from the illustration in FIG. 13 that the space between the tooth root canal 19 and the outer wall of the tooth 25 decreases toward the base of the tooth when the dental post 310 is threaded into the tooth root canal 19. At that time the tapered apical leading end 323 of the post 310 is closed to the outer wall of the tooth than any other portion of the dental post.]

Figure 13:
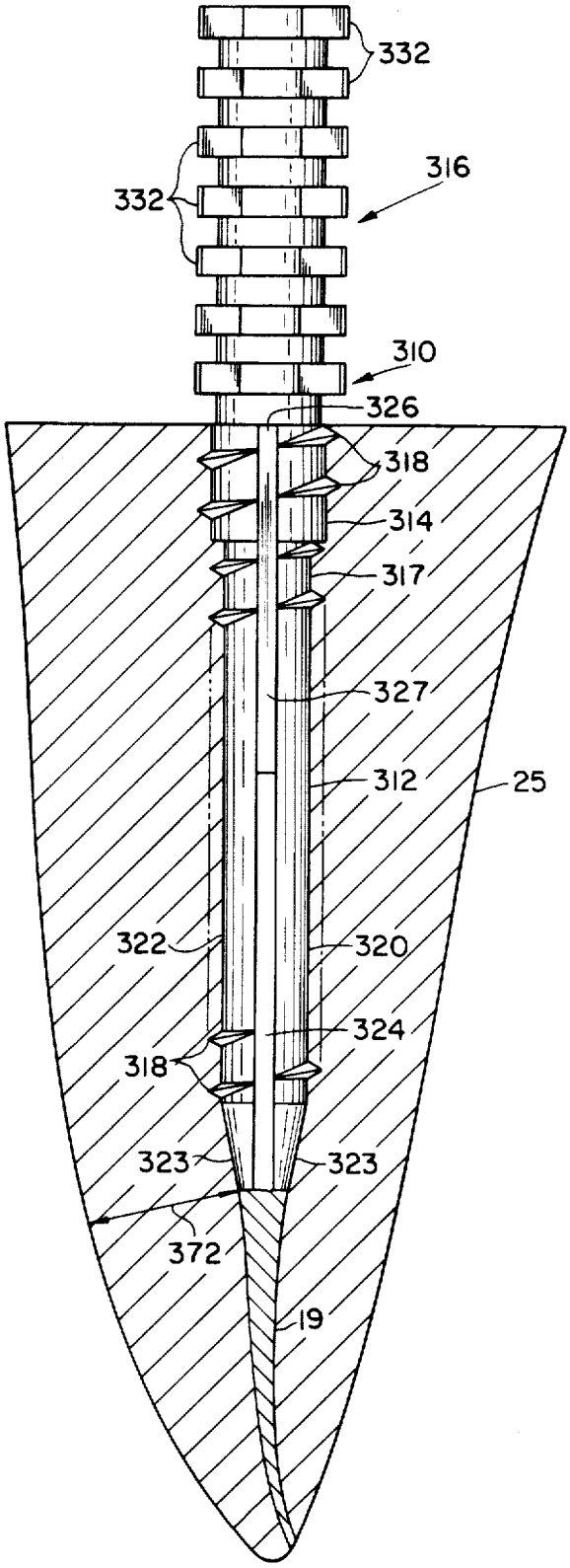
[FIG. 13 is a plan view of the dental post of FIG. 8 threaded fully into a tooth root.]

[If, however, the space between the apical end of the post 310 and the outer wall of the tooth is less than one mm., there is not sufficient wall thickness to sustain and resist those forces that tend to fracture the tooth adjacent the nearest part of the dental post. Therefore, to provide for such minimum tooth thickness and still enable the dental post 310 to enter and be mounted as deep as possible in a tooth so as to add strength to the tooth, the post is tapered as at 323 with an angle corresponding substantially to that of the leading end of the root canal as formed by the drill and tap used to open the root canal and to thread the same. By so doing, the deepest end 323 of the dental post 310 is always spaced at least the distance of one mm. from the adjacent outer wall of the tooth 25 as is illustrated in FIG. 13 by the double headed arrow 372.]

While there have been shown and described and pointed out the fundamental novel features of the invention as applied to preferred embodiments thereof, it will be understood that various omissions and substitutions and changes in the form and details of the device illustrated and in its operation may be made by those skilled in the art without departing from the spirit of the invention. It is the intention, therefore, to be limited only as indicated by the scope of the claims appended hereto.

What is claimed is:

1. A dental post for thread cutting insertion into a tooth root comprising a stem having a space defined therein dividing a lengthwise portion of said stem into a plurality of relatively spaced legs, self-tapping threads on said legs and stem to cut and form a thread in the tooth root as said stem is threadedly inserted thereinto, said legs being movable relative to each other at said space during the thread cutting insertion of said stem into the tooth root to absorb the application of at least lateral fracturing forces to the walls of the tooth root, and said space including vent means extending from the insertion end of said stem to at least beyond the tooth root to vent the insertion end of said stem to the atmosphere to vent the build-up of tooth fracturing forces from between said stem and tooth root during the threading of said stem into the tooth root.

2. A dental post as in claim 1, said space including a slot defined in and extending diametrically through said stem.

[3. A dental post as in claim 2, said space including a groove coextensive with and forming a vent continuation of said slot.]

4. A dental post as in claim 1,
anchor means unitary with said stem for anchoring a dental crown thereto.

5. A dental post as in claim 1,
a body of greater width than said stem unitarily joined coextensive with and between said stem and anchor means and having a self-tapping thread coextensive with said threads on said legs and stem.

6. A dental post as in claim 5,
said body having a portion adjacent said stem and being rounded to obviate fracture of the tooth during engagement with the same when the stem and body are threaded into the tooth root.

7. A tooth root as in claim 4,
said stem being enlarged along the length thereof between said legs and anchor means.

8. A dental post as in claim 4,
said self-tapping threads extending between an entry portion of said stem and said anchor means.

9. A dental post as in claim 4,
said anchor means extending in a direction opposite said stem and having a plurality of relatively spaced means to which a dental crown is cemented.

10. A dental post as in claim 1,
said walls of said stem being substantially parallel and of a substantially continuous diameter.

11. A dental post for use in a tooth root canal comprising
a stem having a lengthwise extent for insertion into a tooth root,
a space including a slot in a portion of the lengthwise extent of said stem extending from the insertion end of said stem to form a plurality of relatively spaced movable legs,
a tooth root cutting thread on said stem extending about and along said legs to facilitate the thread cutting insertion of said lengthwise extent into the tooth root by cutting the tooth root and forming therein a thread corresponding to the cutting thread of said stem during the threading insertion of said stem into the tooth root,
said legs, moving relative to each other during the threading insertion to absorb forces that result from the cutting and forming of the threads in the tooth root to prevent the application of such forces to otherwise fracture the tooth root,
and said space venting hydrostatic forces in the tooth root to the atmosphere to avoid the application of such hydrostatic fracturing forces to the tooth.

12. A dental post as in claim 11,
said stem being substantially circular and of the same diameter throughout the insertion length thereof.

13. A dental post as in claim 4,
anchor means on the distal end of said dental post opposite said stem for anchoring a dental crown thereto.

14. A dental post as in claim 13,
an enlarged body on said stem between said stem and anchor means and having a continuation of said cutting thread thereon.

[15. A dental post as in claim 11,
the insertion end of said legs being tapered to correspond to the taper of the tooth root canal to provide for bulk support thereat and at least a minimum of tooth thickness therebetween for sufficient bulk and strength to resist fracture of the tooth thereat.]

* * * * *

UNITED STATES PATENT AND TRADEMARK OFFICE

CERTIFICATE OF CORRECTION

PATENT NO. : Re. 31,948

DATED : July 16, 1985

INVENTOR(S) : Allan S. Deutsch and Barry L. Musikant

It is certified that error appears in the above-identified patent and that said Letters Patent are hereby corrected as shown below:

Claim 13, line 1, change "4" to --11--

Signed and Sealed this

*Twenty-second* Day of *October 1985*

[SEAL]

*Attest:*

DONALD J. QUIGG

*Attesting Officer*

*Commissioner of Patents and Trademarks—Designate*